United States Patent [19]

Cavalla et al.

[11] 4,028,352
[45] June 7, 1977

[54] BENZAMIDOPIPERIDINE DERIVATIVES

[75] Inventors: John Frederick Cavalla, Isleworth; John Leheup Archibald, Windsor, both of England

[73] Assignee: John Wyeth & Brother Limited, Maidenhead, England

[22] Filed: Apr. 20, 1976

[21] Appl. No.: 678,773

Related U.S. Application Data

[60] Division of Ser. No. 564,509, April 2, 1975, Pat. No. 3,992,389, which is a continuation-in-part of Ser. No. 323,684, Jan. 15, 1973, abandoned, which is a continuation of Ser. No. 175,345, Aug. 26, 1971, abandoned.

[30] Foreign Application Priority Data

Sept. 30, 1970 United Kingdom ............ 42090/70
July 22, 1971 United Kingdom ............ 34376/71
Dec. 21, 1972 United Kingdom ............ 59144/72

[52] U.S. Cl. .................. 260/240 R; 260/240 D; 260/240 K; 260/293.77; 424/267
[51] Int. Cl.² .................................. C07D 211/06
[58] Field of Search ...... 260/240 R, 240 K, 293.77, 260/240 D

[56] References Cited

UNITED STATES PATENTS

| | | | |
|---|---|---|---|
| 2,712,023 | 6/1955 | Adamson | 260/240 R |
| 3,010,965 | 11/1961 | Elpern | 260/240 R |
| 3,553,225 | 1/1971 | Kaiser et al. | 260/240 K |
| 3,661,976 | 5/1972 | Wittle | 260/240 R |

*Primary Examiner*—Arthur P. Demers
*Attorney, Agent, or Firm*—Arthur E. Wilfond

[57] ABSTRACT

A group of heterocyclic compounds useful in the treatment of disorders and diseases of the cardiovascular system is described. These compounds are piperidine compounds linked by the nitrogen atom to a halogen-substituted or unsubstituted phenyl radical through the intermediary of a

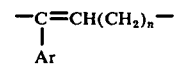

group wherein $n$ is an integer from 1 to 4, and Ar represents phenyl or halophenyl. The piperidine rings are further substituted by a benzamido residue.

3 Claims, No Drawings

BENZAMIDOPIPERIDINE DERIVATIVES

This invention relates to novel heterocyclic compounds, to processes for their manufacture and to novel intermediates. This application is a divisional of U.S. Ser. No. 564,509 filed Apr. 2, 1975 which became U.S. Pat. No. 3,992,389, Nov. 16, 1976 and which is a continuation-in-part of Ser. No. 323,684 filed Jan. 15, 1973 now abandoned which was itself a continuation of Ser. No. 175,345 filed Aug. 26, 1971 now abandoned.

In its broadest aspect the present invention provides a heterocyclic compound of the general formula

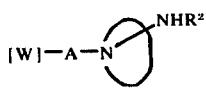  (I)

in which

represents a ring system of the general formula

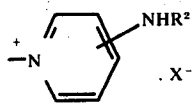 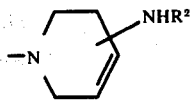

II(a)      II(b)

or

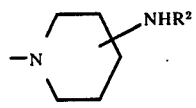

II(c)

W represents a radical of the formula $Ar_2C=CH-$, wherein Ar is a phenyl or a halophenyl radical, A represents a lower alkylene radical of 1-4 carbon atoms, $R^2$ represents the group —COR, where R represents phenyl, $X^-$ is an anion, and the acid addition and quaternary ammonium salts of those compounds wherein

is a ring system of formula II(b) or II(c).

The compounds of formula (I) which have a ring system of formula II(b) or II(c) wherein W and A are as defined above, R represents phenyl and the pharmaceutically acceptable acid addition salts thereof exhibit pharmacological activity in particular action on the cardiovascular system (such as hypotensive and/or anti-hypertensive activity) when tested on warm-blooded animals.

In addition to having useful pharmaceutical properties as mentioned above the novel compounds of the invention are intermediates for the preparation of corresponding compounds of formula I where W is $Ar_2CHCH_2-$. These compounds which exhibit pharmacological activity, e.g., hypotensive activity are described and claimed in our U.S. Ser. No. 564,509 (filed Apr. 2, 1975) the disclosure of which is incorporated herein by reference.

In a preferred aspect the invention provides a compound selected from the group consisting of (A) heterocyclic compounds of the formula

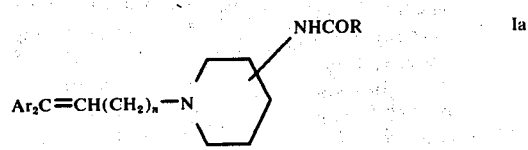  Ia in which n denotes an integer from 1 to 4, Ar represents phenyl or halophenyl and R represents phenyl; and (B) the pharmaceutically acceptable acid addition and quaternary ammonium salts thereof.

In formula Ia, Ar may be phenyl or halophenyl where the halogen is for example fluorine, chlorine or bromine.

Examples of acid addition salts are those formed from inorganic and organic acids in particular pharmaceutically acceptable acid addition salts such as the sulphate, hydrochloride, hydrobromide, hydroiodide, nitrate, phosphate, sulphonate (such as the methane-sulphonate and p-toluene-sulphonate), acetate, maleate, fumarate, tartrate and formate.

The compounds of general formula (I) can be prepared in a number of ways by building up the molecule from suitable starting materials in known manner. Such processes applied to the preparation of the novel compounds of formula (I) are included in the scope of the invention.

One method of preparation of compounds of general formula (I) in which $R^2$ is the —COR group comprises reacting a compound of the general formula

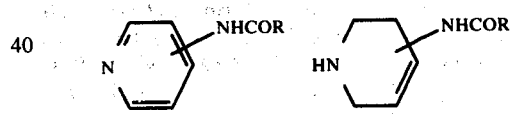

III(a)      III(b)

or

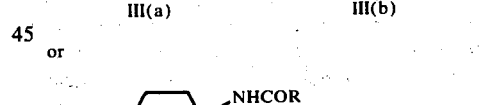

III(c)

with an alkylating or acylating agent of the general formula

 [W]—A—Y      (IV)

where R, W and A have the meanings already defined and Y is a halogen atom or an equivalent replaceable atom or radical, for example an organic sulphonyl radical such as tosyl radical.

The compounds of general formula (IV) are known compounds or can be made following the methods known for preparing compounds of these types. The starting materials of general formulae III(a), III(b) and III(c) can generally be made by acylating a corresponding amino compound of the general formula

(VIII)

and if necessary reducing the ring system to the corresponding tetrahydropyridine or piperidine ring. The starting material of general formula III(c) is preferably prepared by either (i) forming the oxime of an N-benzyl-4-piperidone, reducing to give the 4-amino compound, acylating the amino group and then hydrogenolysing the benzyl residue, or (ii) treating the pyridine of formula

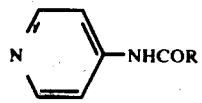
(IX)

with a benzyl halide, for example benzyl chloride to give the quaternary salt, reducing with an alkali metal borohydride to give the corresponding N-benzyl-tetrahydropyridine which is further subjected to concomitant de-benzylation and reduction of the 3,4-double bond by catalytic hydrogenation, or (iii) catalytic hydrogenation of compound (IX) in the presence of acetic anhydride to give

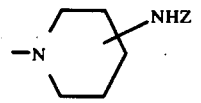
(X)

and then selectively hydrolyzing the acetyl group.

A second general method of preparation of compounds of formula (I) in which $R^2$ is the —COR group, comprises reacting a compound of formula (I) in which $R^2$ is a hydrogen atom, with either a reactive derivative of an acid of general formula R.COOH (where R is aryl, or cycloalkyl). As a reactive derivative of the acid of formula R.COOH used in the process described above, we have found it preferable usually to use a halide (for example the chloride or bromide) or an anhydride. Other examples of reactive derivatives of the acid R.COOH which may be used are the acid azide, mixed anhydrides and active esters. Furthermore, the compounds of formula (I) in which $R^2$ is the —COR group may also be prepared by treating a compound of formula (I) in which $R^2$ is a hydrogen atom with the acid R.COOH in the presence of a known condensing agent (for example, a carbodiimide), or by first activating the amino function (for example, by forming the phosphazo derivative) and then reacting with the acid R.COOH. In connection with the introduction of the —COR group into a compound of formula (I) in which $R^2$ is a hydrogen atom, reference may be made to "Chemistry of the Amino Acids" by Greenstein and Winitz (John Wiley & Sons, Inc., Publishers, 1961) at pages 782–883 and 943–1108.

When it is desired to prepare a compound of general formula (I) wherein $R^2$ is a hydrogen atom, a corresponding compound of formula

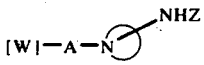
(XII)

wherein W has the meaning defined in connection with formula (I),

represents a ring system of formula

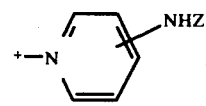   

XIII(a)           XIII(b)

or

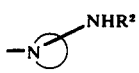

XIII(c)

and Z is a protecting group known in the art for the protection of the amino function and A has the meanings defined in connection with formula I, is subjected to hydrolysis, hydrogenolysis or some other reaction known in the art for the removal of the protecting group Z. As examples of Z, mention is made of those wherein Z is the group —COR and R is lower alkyl, lower alkoxy and aryloxy (particularly methyl, ethoxy and phenoxy respectively) or aryl. Other examples of Z are benzyl, p-toluene-sulphonyl, phthalyl, trityl, trifluoroacetyl, formyl and benzyl-sulphonyl. Reference may be made to the review of protecting groups in Advances in Organic Chemistry, 3, 191–294 (Interscience Publishers 1963), and also to Chemistry of the Amino Acids by Greenstein and Winitz, Vol. 2, pages 885–924 (John Wiley & Sons, Inc., 1961). The compounds of general formula (XII) can be prepared following the information already given but using the appropriate acylating agent or other reagent to introduce the group Z.

A still further aspect of the invention is the provision of a further process for the preparation of compounds of general formula (I) in which

represents a ring system of formula II(b) or II(c), W and $R_1$ have the meanings defined in connection with formula (I), $R^2$ is the group —COR, R has the meanings defined in connection with formula (I) and A is as defined in connection with formula I, and wherein the process consists of reacting a compound of the general formula

[W]—A—OH          (XVI)

(in which W, and A have the meanings defined immediately above) with a compound of formula III(b) or III(c) (in which $R^2$ has the meaning defined immediately above).

The reaction is preferably carried out in the presence of a catalyst, for example Raney Nickel. An organic solvent, which is inert under the reaction conditions, is usually used for example xylene, toluene or benzene. Preferably the reaction is carried out by heating the reactants under reflux in a water-immiscible organic solvent, for example xylene, and removing the water formed during the reaction by azeotropic distillation. If necessary, reactive substituent groups can be blocked during a reaction and released later.

The reactions outlined above usually are carried out in a solvent which is inert under the reaction conditions. The most suitable solvent system is chosen and varies depending on the particular reactants being employed. If necessary heating the reactants in solution under reflux can be carried out, and if necessary heating under high pessures may also be used.

Once a compound of general formula (I) has been prepared, then if necessary one or more substituents in the molecule may be converted to another substituent each within its own meanings specified in connection with formula (I).

If a compound of formula (I) is produced in which $R^2$ is the —COR group, if necessary this may be hydrolyzed to the compound of formula (I) in which $R^2$ is a hydrogen atom and which may then be reacted to give a compound of formula (I) in which $R^2$ is a different —COR group.

Compounds of formula I where W is ArC=CH— may be converted into corresponding compounds of formula I wherein W is $Ar_2CHCH_2$— by catalytic hydrogenation. The hydrogenation may be carried out with hydrogen in the presence of a hydrogenation catalyst such as a palladium or platinum catalyst. A suitable catalyst is palladium on carbon. If the compound of formula I has a pyridine ring of formula II(a) or a tetrahydropyridine ring of formula II(b) the hydrogenation can be carried out so as to reduce both the ethylenic bond and the ring system.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halides in the presence or absence of a solvent.

As already mentioned, the pharmaceutical compositions of the invention contain as active ingredients a compound of formula (I) as hereinbefore defined, which may be micronised. In addition to the active ingredient, said comositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavoring agents, lubricants, solubilizers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention. Example 1 is a reference example.

EXAMPLE 1 (Reference Example)

4-Benzamido-1-[4-(4-methoxyphenyl)-4-oxobutyl]-piperidine

4-Benzamidopiperidine (4.086 g., 0.02 mole), 4-(4-chloro-1-oxobutyl)methoxybenzene (4.245 g., 0.02 mole) and finely ground anhydrous potassium carbonate (4.146 g., 0.03 mole) were mixed and heated on a steam bath for 1 hour. The solid obtained was stirred in water at 60° for 1 hour, the title compound was filtered off, washed well with water and ether to give 3.82 g. This was dissolved in hot absolute ethanol, the solution was acidified with ethanolic hydrogen chloride and cooled to give the hydrochloride of the title compound (3.54 g., 41%) m.p. 224.8°.

$C_{23}H_{28}N_2O_3.HCl.H_2O$ requires C, 63.51; H, 7.18; N, 6.44. Found: C, 63.50; H, 6.84; N, 6.35%.

The product exhibited hypotensive activity in standard test procedures.

EXAMPLE 2

4-(4-Benzamidopiperid-1-yl)-1,1-(di-p-fluorophenyl)-but-1-ene

Using the method of Example 1, 4-benzamidopiperidine (2.687 g.) was alkylated with 1,1-(di-p-fluorophenyl)-4-chlorobut-1-ene (3.784 g.) to give the title product as the hydrochloride, hemihydrate in 28% yield (1.821 g.) m.p. 272.7° C.

$C_{28}H_{28}F_2N_2O.HCl.\frac{1}{2}H_2O$ requires C, 68.34; H, 6.15; N, 5.69. Found: C, 68.29; H, 6.19; N, 5.71%.

The product exhibits hypotensive activity and is an intermediate for the compound of the next example.

EXAMPLE 3

4-(4-Benzamidopiperid-1-yl)-1,1-(di-p-fluorophenyl)-butane 4-(4-Benzamidopiperid-1-yl)-1,1-(di-p-fluorophenyl)-but-1-ene, hydrochloride (885 mg.) was hydrogenated using 10% palladium charcoal (1.0 g.) at 50 p.s.i. and 50° in methanol (120 ml.) containing a few drops of concentrated hydrochloric acid for 24 hours. The catalyst was filtered off and the filtrate was evaporated to give a residue which gave the hydrochloride of the title compound (277 mg., 31.2%) m.p. 256.8°, on treatment with ethanolic hydrogen chloride and ether.

$C_{28}H_{30}F_2N_2O.HCl$ requires C, 69.35; H, 6.44; N, 5.78. Found: C, 69.34; H, 6.79; N, 5.95%.

The product exhibited hypotensive activity in a standard test procedure.

EXAMPLE 4

4-(4-Benzamidopiperid-1-yl)-1,1-diphenylbut-1-ene

Using the procedure of Example 1 over a period of 20 hours, 4-benzamidopiperidine (7.473 g.) was alkylated with 1,1-diphenyl-4-chlorobut-1-ene (8.879 g.). The title compound was filtered off after addition of water and ether to the reaction mixture and a further crop was obtained from the ether washings. Conversion of the combined product to the hydrochloride using ethanolic hydrogen chloride gave 6.308 g. (38.2%). m.p. 220°-230° (dec.).

$C_{28}H_{30}N_2O.HCl.\frac{1}{4}H_2O$ requires C, 74.46; H, 7.03; N, 6.20. Found: C, 74,77; H, 7.26; N, 6.14%.

The product exhibited hypotensive activity in a standard test procedure and is an intermediate for the compound of the next example.

EXAMPLE 5

4-(4-Benzamidopiperid-1-yl)-1,1-diphenyl butane

Using the procedure of Example 3, 4-(4-Benzamidopiperid-1-yl)-1,1-diphenylbut-1-ene (4.105 g., 0.01 mole) was reduced to the title compound using 500 mg. of 10% palladium-charcoal. The hydrochloride of the product was obtained using the method of Example 1 in 62.4% yield (2.800 g.) m.p. 269.2°.

$C_{28}H_{32}N_2O.HCl$ requires C, 74.90 H, 7.41; N, 6.24. Found: C, 74.55; N, 7.47; N, 6.15%.

The product exhibited hypotensive activity in a standard test procedure.

The invention includes a method of relieving disorders and diseases of the cardiovascular system in a manual which comprises administering to said mammal a therapeutically effective amount of a heterocyclic compound of general formula (I)

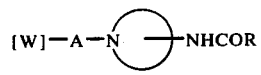

in which

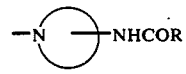

represents a ring system of general formula

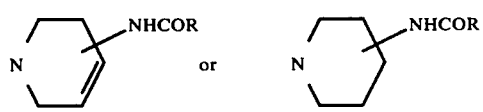

W represents a radical of the formula $Ar_2C=CH-$, wherein Ar is a phenyl or halophenyl radical, A represents a lower alkylene radical containing 1-4 carbon atoms, R represents a phenyl radical and the pharmaceutically acceptable acid addition salts thereof.

Tests for action on the cardiovascular system were conducted according to one of the following procedures:

HYPOTENSIVE AND/OR ANTI-HYPERTENSIVE ACTIVITY

Method 1 (Rat)

Rats were anaesthetized with pentobarbitone sodium (60 mg/kg) and the jugular vein, trachea and carotid artery were cannulated. The test compound was given intravenously at 15 min. intervals (dose range 0.8–25.6 mg/kg cumulative) and blood pressure and heart rate were recorded via the carotid artery at 30 second and 15 minutes after administration. The production of a fall of 30 mm. mercury in diastolic pressure from control values was considered to be significant hypotensive activity. A decrease in heart rate of more than 30% from control values was considered to be significant bradycardia.

Method 1 (Cat)

Cats were anaesthetized with pentobarbitone sodium (30 mg/kg) and the cephalic vein, femoral and carotid arteries and trachea were cannulated. The carotid cannula was introduced into the left ventricle and the femoral cannula into the aorta. Blood pressure and heart rate were recorded from the aortic cannula and left centricular pressure from the carotid cannula. The test compounds were administered intraveneously (0.1–25.6 mg/kg).

Method 2 (hypertensive rats)

Male or female rats are rendered hypertensive by applying a figure of 8 ligature around one kidney and contralateral nephrectomy. Blood pressure stabilizes at a hypertensive level after 6 weeks. Systolic pressure is measured indirectly using a Decker Caudal Plethysmograph. A control group of rats is run with each group treated with drug. Each group usually consists of six rats. Drugs are usually administered by the IP or oral routes. Pressures are read prior to drug administration and at 2 and 24 hours thereafter.

Activity in either method 1 (rats or cats) or method 2 was considered to indicate hypotensive activity.

The following results were obtained with compounds of the invention (examples 2 and 4) and the products into which they can be converted (examples 3 and 5).

| Compound of Example | Hypotensive Activity [a] | Anti-hypertensive Activity [b] |
| --- | --- | --- |
| 2 | + | |
| 3 | +++ | + |
| 4 | ++ | + |
| 5 | ++ | + |

Key
[a] Cumulative iv doses producing a fall in diastolic blood pressure of 30mm or more, sustained for at least 15 minutes: 1.6 or 3.2 mg/kg +++; 6.4 or 12.8 mg/kg ++; 25.6 mg/kg +.
[b] Falls in systolic blood pressure 2 hours after oral dose of 40 mg/kg: 30–15mm, +.

We claim:

1. A compound selected from the group consisting of (A) heterocyclic compounds of formula Ia

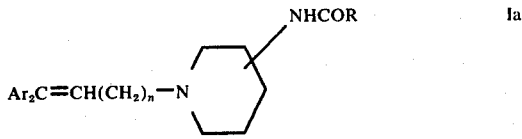

where $n$ denotes an integer from 1 to 4, Ar represents phenyl or monohalophenyl and R represents phenyl and (B) the pharmaceutically acceptable acid addition and quaternary ammonium salts thereof.

2. A compound as claimed in claim 1 which is 4-(4-Benazmidopiperid-1-yl)-1,1-(di-p-fluorophenyl)but-1-ene or a pharmaceutically acceptable acid addition salt thereof.

3. A compound as claimed in claim 1, which is 4-(4-benzamidopiperid-1-yl)-1,1-diphenylbut-1-ene or a pharmaceutically acceptable acid addition salt thereof.

* * * * *